(12) United States Patent
Lentner et al.

(10) Patent No.: US 11,331,125 B1
(45) Date of Patent: May 17, 2022

(54) LOW PROFILE ROD-TO-ROD COUPLER

(71) Applicant: Ortho Inventions, LLC, Palm Beach Gardens, FL (US)

(72) Inventors: Greg Lentner, Maumee, OH (US); John E. Hammill, Sr., Maumee, OH (US)

(73) Assignee: Ortho Inventions, LLC, Palm Beach Gardens, FL (US)

( * ) Notice: Subject to any disclaimer, the term of this patent is extended or adjusted under 35 U.S.C. 154(b) by 0 days.

(21) Appl. No.: 17/496,471

(22) Filed: Oct. 7, 2021

(51) Int. Cl.
*A61B 17/70* (2006.01)
(52) U.S. Cl.
CPC ................. *A61B 17/7052* (2013.01)
(58) Field of Classification Search
CPC ............ A61B 17/7043; A61B 17/7049; A61B 17/705; A61B 17/7052; A61B 17/8023; A61B 17/7025; A61B 17/7047; A61B 17/7073
See application file for complete search history.

(56) References Cited

U.S. PATENT DOCUMENTS

| | | |
|---|---|---|
| 4,641,636 A | 2/1987 | Cotrel |
| 4,771,767 A | 9/1988 | Steffee |
| 4,805,602 A | 2/1989 | Puno et al. |
| 4,946,458 A | 8/1990 | Harms et al. |
| 4,998,936 A | 3/1991 | Mehdian |
| 5,005,562 A | 4/1991 | Cotrel |
| 5,034,011 A | 7/1991 | Howland |
| 5,042,982 A | 8/1991 | Harms et al. |
| 5,084,049 A | 1/1992 | Asher et al. |
| 5,092,866 A | 3/1992 | Breard et al. |
| 5,092,867 A | 3/1992 | Harms et al. |
| 5,092,893 A | 3/1992 | Smith |
| 5,129,388 A | 7/1992 | Vignaud et al. |
| 5,154,718 A | 10/1992 | Cozad et al. |
| 5,176,680 A | 1/1993 | Vignaud et al. |
| 5,196,013 A | 3/1993 | Harms et al. |
| 5,207,678 A | 5/1993 | Harms et al. |
| 5,234,431 A | 8/1993 | Keller |
| 5,261,907 A | 11/1993 | Vignaud et al. |
| 5,275,600 A * | 1/1994 | Allard ................ A61B 17/7052 606/252 |

(Continued)

FOREIGN PATENT DOCUMENTS

| | | |
|---|---|---|
| WO | WO2007130007 | 11/2007 |
| WO | WO2010045219 | 4/2010 |
| WO | WO2011057178 | 5/2011 |

*Primary Examiner* — Lynnsy M Summitt
(74) *Attorney, Agent, or Firm* — McHale & Slavin, P.A.

(57) ABSTRACT

A low profile rod-to-rod cross-connector formed from an outer bar member having a first end forming a receptacle and a second end available for coupling to a first spinal rod. An inner bar having a unidirectional insertion end is slidably insertable into the receptacle, and a second end is available for coupling to a second spinal rod; the insertion end having a centrally disposed slot bifurcating the insertion end. A locking member is positioned in the centrally disposed slot, wherein placement of the locking member in the first position permits movement of the insertion end within the receptacle, and placement of the locking member in the second position results in splaying the left arm and right arm to frictionally engage an inner sidewall of the receptacle.

19 Claims, 5 Drawing Sheets

(56) References Cited

U.S. PATENT DOCUMENTS

| | | | |
|---|---|---|---|
| 5,306,275 A | 4/1994 | Bryan | |
| 5,312,405 A | 5/1994 | Korotko et al. | |
| 5,330,473 A | 7/1994 | Howland | |
| 5,375,823 A | 12/1994 | Navas | |
| 5,387,213 A | 2/1995 | Breard et al. | |
| 5,397,363 A | 3/1995 | Gelbard | |
| 5,403,314 A | 4/1995 | Currier | |
| 5,439,463 A * | 8/1995 | Lin | A61B 17/7052 606/252 |
| 5,466,237 A | 11/1995 | Byrd, III et al. | |
| 5,474,555 A | 12/1995 | Puno et al. | |
| 5,478,340 A | 12/1995 | Kluger | |
| 5,480,401 A | 1/1996 | Navas | |
| 5,498,263 A | 3/1996 | DiNello et al. | |
| 5,501,684 A | 3/1996 | Schlapfer et al. | |
| 5,505,731 A | 4/1996 | Tornier | |
| 5,522,816 A | 6/1996 | DiNello et al. | |
| 5,536,268 A | 7/1996 | Griss | |
| 5,540,688 A | 7/1996 | Navas | |
| 5,545,163 A | 8/1996 | Miller et al. | |
| 5,545,166 A | 8/1996 | Howland | |
| 5,562,661 A | 10/1996 | Yoshimi et al. | |
| 5,569,246 A | 10/1996 | Ojima et al. | |
| 5,601,554 A | 2/1997 | Howland et al. | |
| 5,607,425 A | 3/1997 | Rogozinski | |
| 5,624,442 A | 4/1997 | Mellinger et al. | |
| 5,630,816 A | 5/1997 | Kambin | |
| 5,643,264 A | 7/1997 | Sherman et al. | |
| 5,645,544 A | 7/1997 | Tai et al. | |
| 5,665,122 A | 9/1997 | Kambin | |
| 5,667,508 A | 9/1997 | Errico et al. | |
| 5,669,910 A * | 9/1997 | Korhonen | A61B 17/7052 606/151 |
| 5,669,911 A | 9/1997 | Errico et al. | |
| 5,672,176 A | 9/1997 | Biedermann et al. | |
| 5,676,665 A | 10/1997 | Bryan | |
| 5,676,703 A | 10/1997 | Gelbard | |
| 5,681,311 A | 10/1997 | Foley et al. | |
| 5,688,272 A | 11/1997 | Montague et al. | |
| 5,688,275 A | 11/1997 | Koros et al. | |
| 5,690,630 A | 11/1997 | Errico et al. | |
| 5,693,053 A | 12/1997 | Estes | |
| 5,702,393 A | 12/1997 | Pfaifer | |
| 5,704,936 A | 1/1998 | Mazel | |
| 5,716,355 A | 2/1998 | Jackson et al. | |
| 5,725,527 A | 3/1998 | Biedermann et al. | |
| 5,735,852 A | 4/1998 | Amrein et al. | |
| 5,776,135 A | 7/1998 | Errico et al. | |
| 5,800,435 A | 9/1998 | Errico et al. | |
| 5,863,293 A | 1/1999 | Richelsopf | |
| 5,873,878 A | 2/1999 | Harms et al. | |
| 5,928,232 A | 7/1999 | Howland et al. | |
| 5,928,237 A | 7/1999 | Farris et al. | |
| 5,938,663 A | 8/1999 | Petreto | |
| 5,944,719 A | 8/1999 | Leban | |
| 5,944,720 A | 8/1999 | Lipton | |
| 5,947,966 A | 9/1999 | Drewry et al. | |
| 5,951,555 A | 9/1999 | Rehak et al. | |
| 5,954,722 A | 9/1999 | Bono | |
| 5,954,725 A | 9/1999 | Sherman et al. | |
| 5,961,516 A | 10/1999 | Graf | |
| 5,980,521 A | 11/1999 | Montague et al. | |
| 5,980,523 A | 11/1999 | Jackson | |
| 6,004,322 A | 12/1999 | Bernstein | |
| 6,030,389 A | 2/2000 | Wagner et al. | |
| 6,063,089 A | 5/2000 | Errico et al. | |
| 6,074,391 A | 6/2000 | Metz-Stavenhagen et al. | |
| 6,083,226 A | 7/2000 | Fiz | |
| 6,113,600 A | 9/2000 | Drummond et al. | |
| 6,136,003 A | 10/2000 | Hoeck et al. | |
| 6,139,548 A | 10/2000 | Errico et al. | |
| 6,171,311 B1 | 1/2001 | Richelsoph | |
| 6,179,838 B1 | 1/2001 | Fiz | |
| 6,187,005 B1 | 2/2001 | Brace et al. | |
| 6,190,388 B1 | 2/2001 | Michelson et al. | |
| 6,217,578 B1 | 4/2001 | Crozet et al. | |
| 6,224,598 B1 | 5/2001 | Jackson | |
| 6,234,705 B1 | 5/2001 | Troxell | |
| 6,238,396 B1 | 5/2001 | Lombardo | |
| 6,241,730 B1 | 6/2001 | Alby | |
| 6,264,658 B1 | 7/2001 | Lee et al. | |
| 6,267,765 B1 * | 7/2001 | Taylor | A61B 17/7007 606/86 A |
| 6,273,914 B1 | 8/2001 | Papas | |
| 6,280,445 B1 | 8/2001 | Morrison et al. | |
| 6,283,967 B1 | 9/2001 | Troxell et al. | |
| 6,296,644 B1 | 10/2001 | Saurat et al. | |
| 6,306,137 B2 | 10/2001 | Troxell | |
| 6,325,802 B1 | 12/2001 | Frigg | |
| 6,328,740 B1 | 12/2001 | Richelsoph | |
| 6,328,741 B1 | 12/2001 | Rishelsoph | |
| 6,379,354 B1 | 4/2002 | Rogozinski | |
| 6,402,751 B1 | 6/2002 | Hoeck et al. | |
| 6,402,756 B1 * | 6/2002 | Ralph | A61B 17/8023 606/71 |
| 6,413,258 B1 | 7/2002 | Bernhardt, Jr. | |
| 6,482,207 B1 | 11/2002 | Errico | |
| 6,485,491 B1 | 11/2002 | Farris et al. | |
| 6,524,310 B1 | 2/2003 | Lombardo et al. | |
| 6,554,832 B2 | 4/2003 | Shluzas | |
| 6,602,253 B2 | 8/2003 | Richelsoph et al. | |
| 6,616,668 B2 * | 9/2003 | Altarac | A61B 17/7052 606/252 |
| 6,626,904 B1 | 9/2003 | Jammet et al. | |
| 6,641,583 B2 | 11/2003 | Shluzas et al. | |
| 6,666,867 B2 * | 12/2003 | Ralph | A61B 17/8023 606/71 |
| 6,736,817 B2 | 5/2004 | Troxell et al. | |
| 6,752,807 B2 | 6/2004 | Lin et al. | |
| 6,761,721 B2 | 7/2004 | Burgess et al. | |
| 6,783,526 B1 | 8/2004 | Lin et al. | |
| 6,872,208 B1 | 3/2005 | McBride et al. | |
| 6,875,211 B2 * | 4/2005 | Nichols | A61B 17/7052 606/250 |
| 6,887,241 B1 | 5/2005 | McBride et al. | |
| 6,899,714 B2 | 5/2005 | Vaughan | |
| 6,916,319 B2 | 7/2005 | Munting | |
| 6,958,066 B2 | 10/2005 | Richelsoph et al. | |
| 6,960,212 B2 | 11/2005 | Richelsoph et al. | |
| 7,029,474 B2 | 4/2006 | Richelsoph et al. | |
| 7,066,938 B2 | 6/2006 | Slivka et al. | |
| 7,083,622 B2 | 8/2006 | Simonson | |
| 7,104,993 B2 | 9/2006 | Baynham et al. | |
| 7,122,036 B2 | 10/2006 | Vanacker et al. | |
| 7,137,986 B2 | 11/2006 | Troxell et al. | |
| 7,160,301 B2 | 1/2007 | Cordaro | |
| 7,195,632 B2 * | 3/2007 | Biedermann | A61B 17/645 606/250 |
| 7,207,992 B2 * | 4/2007 | Ritland | A61B 17/7007 606/86 A |
| 7,406,775 B2 | 8/2008 | Funk et al. | |
| 7,585,314 B2 * | 9/2009 | Taylor | A61B 17/7049 606/250 |
| 7,621,914 B2 * | 11/2009 | Ralph | A61B 17/8023 606/71 |
| 7,678,112 B2 | 3/2010 | Rezach | |
| 7,695,473 B2 * | 4/2010 | Ralph | A61B 17/80 606/71 |
| 7,699,873 B2 | 4/2010 | Stevenson et al. | |
| 7,727,265 B2 * | 6/2010 | Paul | A61B 17/8042 606/281 |
| 7,744,632 B2 * | 6/2010 | Usher | A61B 17/7052 606/250 |
| 7,744,633 B2 * | 6/2010 | Berrevoets | A61B 17/7052 606/253 |
| 7,780,704 B2 * | 8/2010 | Markworth | A61B 17/7052 606/253 |
| 7,789,899 B2 * | 9/2010 | Markworth | A61B 17/7007 606/286 |
| 7,833,248 B2 * | 11/2010 | Markworth | A61B 17/7049 606/253 |
| 7,842,071 B2 * | 11/2010 | Hawkes | A61B 17/7052 606/252 |

(56) References Cited

U.S. PATENT DOCUMENTS

| | | | |
|---|---|---|---|
| 7,901,440 B2* | 3/2011 | Ibrahim | A61B 17/8019 606/282 |
| 7,918,876 B2* | 4/2011 | Mueller | A61B 17/7052 606/251 |
| 8,002,810 B2* | 8/2011 | Osman | A61B 17/8009 606/282 |
| 8,062,339 B2 | 11/2011 | Hammer et al. | |
| 8,262,701 B2* | 9/2012 | Rathbun | A61B 17/7052 606/250 |
| 8,277,489 B2* | 10/2012 | Saidha | A61B 17/7049 606/251 |
| 8,337,532 B1 | 12/2012 | McLean et al. | |
| 8,518,085 B2 | 8/2013 | Winslow et al. | |
| 8,617,213 B2* | 12/2013 | Moore | A61B 17/7052 606/253 |
| 8,758,411 B1 | 6/2014 | Rayon et al. | |
| 8,771,319 B2* | 7/2014 | Prajapati | A61B 17/7052 606/278 |
| 8,777,996 B2 | 7/2014 | Black | |
| 8,920,471 B2* | 12/2014 | Barrus | A61B 17/7052 606/251 |
| 8,920,475 B1 | 12/2014 | Ziemek et al. | |
| 8,961,565 B2* | 2/2015 | Barrus | A61B 17/7052 606/250 |
| 9,028,498 B2* | 5/2015 | Hershgold | A61B 17/8042 606/71 |
| 9,055,982 B2* | 6/2015 | Chind | A61B 17/8042 |
| 9,072,547 B2* | 7/2015 | Harper | A61B 17/7052 |
| 9,072,548 B2* | 7/2015 | Matityahu | A61B 17/8052 |
| 9,101,428 B2* | 8/2015 | Long | A61B 17/80 |
| 9,198,696 B1 | 12/2015 | Bannigan et al. | |
| 9,247,964 B1 | 2/2016 | Shoshtaev | |
| 9,468,467 B2* | 10/2016 | Rathbun | A61B 17/707 |
| 9,668,779 B2* | 6/2017 | Okamoto | A61B 17/7052 |
| 9,724,131 B2 | 8/2017 | Bootwala et al. | |
| 9,763,703 B2* | 9/2017 | Black | A61B 17/7052 |
| 9,770,269 B1 | 9/2017 | Shoshtaev | |
| 9,839,447 B2 | 12/2017 | Triplett et al. | |
| 9,895,174 B2 | 2/2018 | Ozdil et al. | |
| 9,980,755 B2* | 5/2018 | Murray | A61B 17/705 |
| 10,058,432 B2* | 8/2018 | Tacca | A61B 17/7049 |
| 10,136,925 B2 | 11/2018 | Shoshtaev | |
| 10,335,206 B2* | 7/2019 | Nichols | A61B 17/7014 |
| 10,357,288 B2* | 7/2019 | Oberlander | A61B 17/7043 |
| 10,383,663 B2* | 8/2019 | Murray | A61B 17/7004 |
| 10,485,587 B2* | 11/2019 | Nichols | A61B 17/809 |
| 10,758,274 B1* | 9/2020 | Bess | A61B 17/7043 |
| 10,792,077 B2* | 10/2020 | Chen | A61B 17/7067 |
| 11,006,980 B2* | 5/2021 | Kono | A61B 17/7032 |
| 11,109,901 B2* | 9/2021 | Hu | A61B 17/823 |
| 2001/0034521 A1 | 10/2001 | Bailey et al. | |
| 2002/0052603 A1 | 5/2002 | Nichols et al. | |
| 2002/0143330 A1 | 10/2002 | Shluzas | |
| 2002/0136448 A1 | 11/2002 | Vanacker | |
| 2003/0023244 A1 | 1/2003 | Richelsoph et al. | |
| 2003/0028191 A1 | 2/2003 | Shluzas | |
| 2003/0045878 A1 | 3/2003 | Petit et al. | |
| 2003/0060823 A1 | 3/2003 | Bryan | |
| 2003/0149432 A1 | 8/2003 | Frigg et al. | |
| 2003/0153917 A1 | 8/2003 | Richelsoph et al. | |
| 2003/0163133 A1 | 8/2003 | Altarac et al. | |
| 2003/0212398 A1 | 11/2003 | Jackson | |
| 2004/0116928 A1* | 6/2004 | Young | A61B 17/7052 606/253 |
| 2004/0138662 A1 | 7/2004 | Landry et al. | |
| 2004/0147928 A1 | 7/2004 | Landry et al. | |
| 2004/0167521 A1* | 8/2004 | De Windt | A61B 17/8052 606/281 |
| 2004/0260287 A1 | 12/2004 | Ferree | |
| 2005/0010217 A1 | 1/2005 | Dalton | |
| 2005/0070901 A1 | 3/2005 | David | |
| 2005/0080416 A1* | 4/2005 | Ryan | A61B 17/7049 606/252 |
| 2005/0090821 A1 | 4/2005 | Berrevoets et al. | |
| 2005/0192572 A1 | 9/2005 | Abdelgany et al. | |
| 2005/0228326 A1 | 10/2005 | Kalfas et al. | |
| 2005/0228377 A1* | 10/2005 | Chao | A61B 17/7052 606/252 |
| 2005/0228382 A1 | 10/2005 | Richelsoph et al. | |
| 2005/0277923 A1 | 12/2005 | Sweeney | |
| 2005/0288670 A1 | 12/2005 | Panjabi et al. | |
| 2006/0036252 A1 | 2/2006 | Baynham et al. | |
| 2006/0052783 A1 | 3/2006 | Dant et al. | |
| 2006/0052786 A1 | 3/2006 | Dant et al. | |
| 2006/0064091 A1 | 3/2006 | Ludwig et al. | |
| 2006/0064093 A1 | 3/2006 | Thramann et al. | |
| 2006/0058789 A1 | 6/2006 | Kim et al. | |
| 2006/0149229 A1 | 7/2006 | Kwak et al. | |
| 2006/0217718 A1 | 9/2006 | Chervitz et al. | |
| 2006/0229606 A1 | 10/2006 | Clement et al. | |
| 2006/0235393 A1 | 10/2006 | Bono et al. | |
| 2006/0241591 A1* | 10/2006 | Biscup | A61B 17/7047 606/60 |
| 2006/0241596 A1 | 10/2006 | Rezach | |
| 2006/0247624 A1 | 11/2006 | Banouskou et al. | |
| 2006/0264933 A1 | 11/2006 | Baker et al. | |
| 2006/0271045 A1 | 11/2006 | Hubbard et al. | |
| 2006/0282074 A1 | 12/2006 | Renaud et al. | |
| 2006/0282075 A1 | 12/2006 | Labrom et al. | |
| 2006/0282076 A1 | 12/2006 | Labrom et al. | |
| 2006/0282077 A1 | 12/2006 | Labrom et al. | |
| 2006/0282078 A1 | 12/2006 | Labrom et al. | |
| 2006/0282079 A1 | 12/2006 | Labrom et al. | |
| 2007/0049932 A1* | 3/2007 | Richelsoph | A61B 17/7052 606/252 |
| 2007/0055239 A1 | 3/2007 | Sweeney et al. | |
| 2007/0083201 A1 | 4/2007 | Jones et al. | |
| 2007/0149973 A1 | 6/2007 | Clement et al. | |
| 2007/0173829 A1* | 7/2007 | Drewry | A61B 17/7052 606/250 |
| 2007/0173833 A1 | 7/2007 | Butler et al. | |
| 2007/0213721 A1 | 9/2007 | Markworth et al. | |
| 2007/0213723 A1 | 9/2007 | Markworth et al. | |
| 2007/0219556 A1* | 9/2007 | Altarac | A61B 17/7032 606/64 |
| 2007/0233062 A1 | 10/2007 | Berry | |
| 2007/0233090 A1* | 10/2007 | Naifeh | A61B 17/7052 606/258 |
| 2007/0233119 A1 | 10/2007 | Markworth | |
| 2007/0270808 A1 | 11/2007 | Drewry et al. | |
| 2007/0270809 A1 | 11/2007 | Drewry et al. | |
| 2007/0288009 A1 | 12/2007 | Brown et al. | |
| 2008/0021464 A1 | 1/2008 | Morin et al. | |
| 2008/0051780 A1 | 2/2008 | Vaidya et al. | |
| 2008/0071273 A1 | 3/2008 | Hawkes et al. | |
| 2008/0091204 A1 | 4/2008 | Kuiper et al. | |
| 2008/0109039 A1 | 5/2008 | Michielli et al. | |
| 2008/0140075 A1 | 6/2008 | Ensign et al. | |
| 2008/0140134 A1 | 6/2008 | Markworth et al. | |
| 2008/0172093 A1 | 7/2008 | Nilsson | |
| 2008/0177315 A1 | 7/2008 | Usher | |
| 2008/0177323 A1 | 7/2008 | Null et al. | |
| 2008/0221622 A1 | 9/2008 | Triplett et al. | |
| 2008/0255617 A1 | 10/2008 | Cho et al. | |
| 2008/0269742 A1 | 10/2008 | Levy et al. | |
| 2008/0281361 A1* | 11/2008 | Vittur | A61B 17/7067 606/249 |
| 2008/0300630 A1* | 12/2008 | Bonnema | A61B 17/7014 606/246 |
| 2008/0306534 A1 | 12/2008 | Winslow et al. | |
| 2008/0306535 A1 | 12/2008 | Winslow et al. | |
| 2008/0312692 A1 | 12/2008 | Brennan et al. | |
| 2009/0043338 A1 | 2/2009 | Laager et al. | |
| 2009/0062860 A1 | 3/2009 | Frasier et al. | |
| 2009/0071273 A1 | 3/2009 | Velsaco | |
| 2009/0125065 A1 | 5/2009 | Laager et al. | |
| 2009/0171395 A1* | 7/2009 | Jeon | A61B 17/7014 606/257 |
| 2009/0187217 A1 | 7/2009 | Weiman et al. | |
| 2009/0216277 A1 | 8/2009 | Tornier et al. | |
| 2009/0228046 A1* | 9/2009 | Garamszegi | A61B 17/7052 606/278 |

(56) References Cited

U.S. PATENT DOCUMENTS

| | | |
|---|---|---|
| 2009/0264931 A1 | 10/2009 | Miller et al. |
| 2009/0318968 A1 | 12/2009 | Duggal et al. |
| 2010/0087864 A1 | 4/2010 | Klein et al. |
| 2010/0087867 A1 | 4/2010 | Klein et al. |
| 2010/0094345 A1 | 4/2010 | Saidha et al. |
| 2010/0094346 A1 | 4/2010 | Matityahu |
| 2010/0094349 A1 | 4/2010 | Hammer et al. |
| 2010/0160981 A1 | 6/2010 | Butler et al. |
| 2010/0191289 A1 | 7/2010 | Ludwig et al. |
| 2010/0198260 A1 | 8/2010 | Gabelberger et al. |
| 2010/0204733 A1 | 8/2010 | Rathbun et al. |
| 2010/0211100 A1 | 8/2010 | Mack |
| 2010/0268279 A1 | 10/2010 | Gabelberger et al. |
| 2010/0280552 A1 | 11/2010 | Lee |
| 2010/0324599 A1 | 12/2010 | Montello et al. |
| 2011/0022095 A1* | 1/2011 | Fanger ............... A61B 17/7026 606/264 |
| 2011/0034957 A1 | 2/2011 | Biedermann |
| 2011/0046675 A1 | 2/2011 | Barrus et al. |
| 2011/0071569 A1 | 3/2011 | Black |
| 2011/0087287 A1 | 4/2011 | Reeder, Jr. et al. |
| 2011/0106178 A1 | 5/2011 | Schwab |
| 2011/0118786 A1 | 5/2011 | Jang |
| 2011/0184462 A1 | 7/2011 | Gil et al. |
| 2012/0029566 A1 | 2/2012 | Rezach |
| 2012/0035659 A1 | 2/2012 | Barrus et al. |
| 2012/0071926 A1 | 3/2012 | Jani et al. |
| 2012/0101529 A1 | 4/2012 | Ludwig et al. |
| 2012/0130436 A1 | 5/2012 | Haskins et al. |
| 2012/0259369 A1 | 10/2012 | Hammer |
| 2014/0336706 A1* | 11/2014 | Garamszegi ....... A61B 17/7052 606/252 |
| 2017/0035465 A1* | 2/2017 | Robinson ........... A61B 17/7052 |
| 2020/0100816 A1* | 4/2020 | Mundis, Jr. ........ A61B 17/8869 |
| 2020/0146728 A1* | 5/2020 | Daniels .............. A61B 17/7002 |
| 2020/0155200 A1* | 5/2020 | Murray ............. A61B 17/7032 |
| 2020/0337738 A1* | 10/2020 | Harper .............. A61B 17/7035 |
| 2020/0352734 A1* | 11/2020 | Purcell .................. A61F 2/4455 |

* cited by examiner

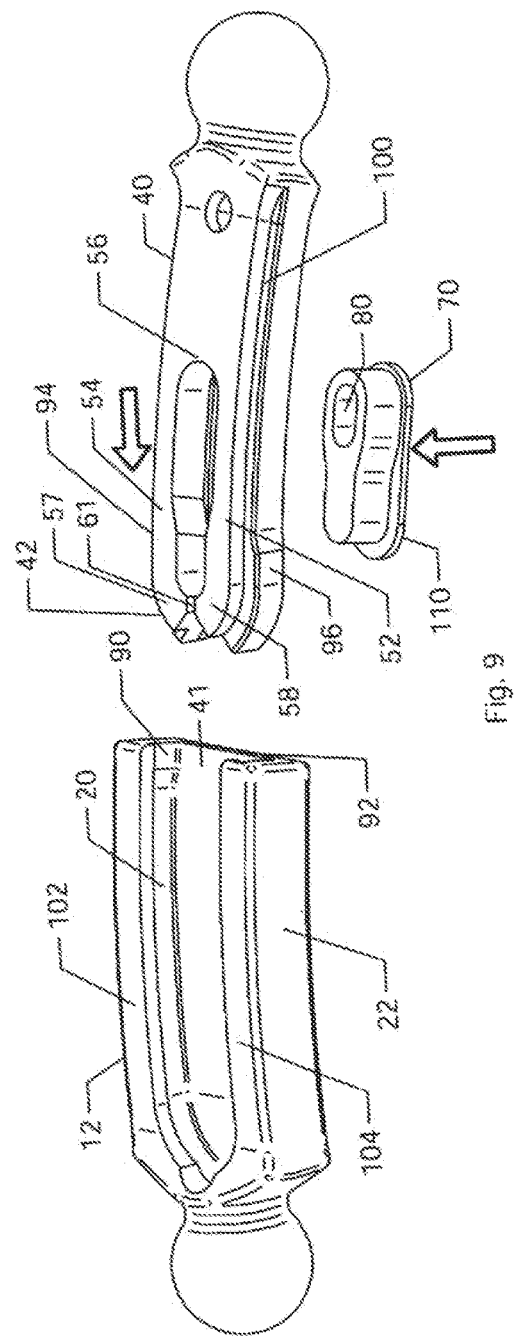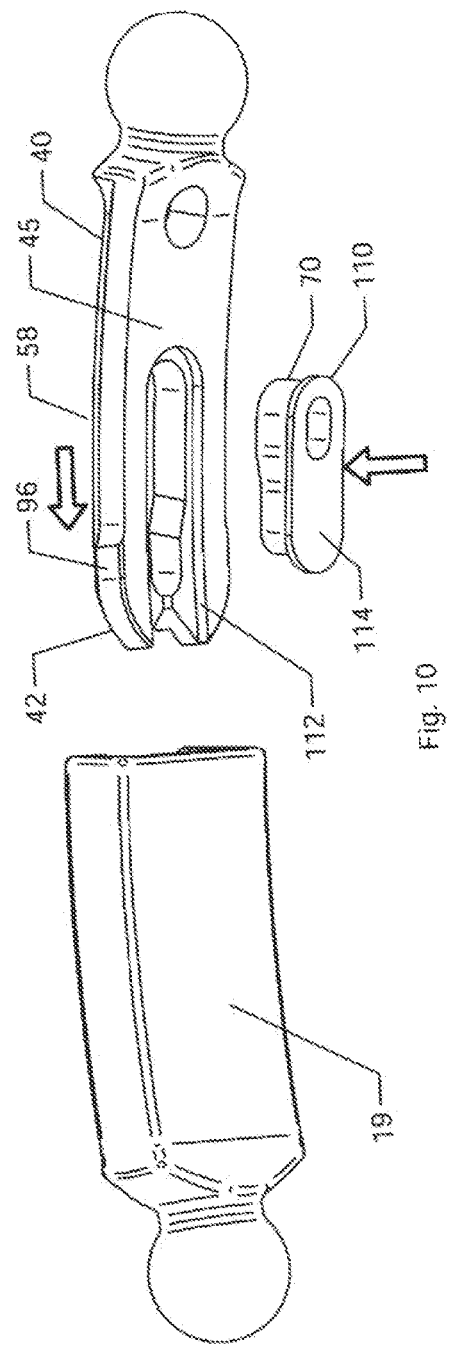

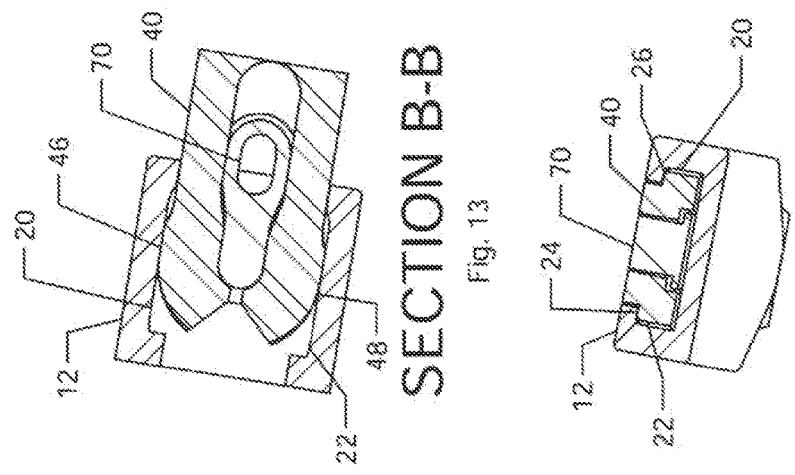
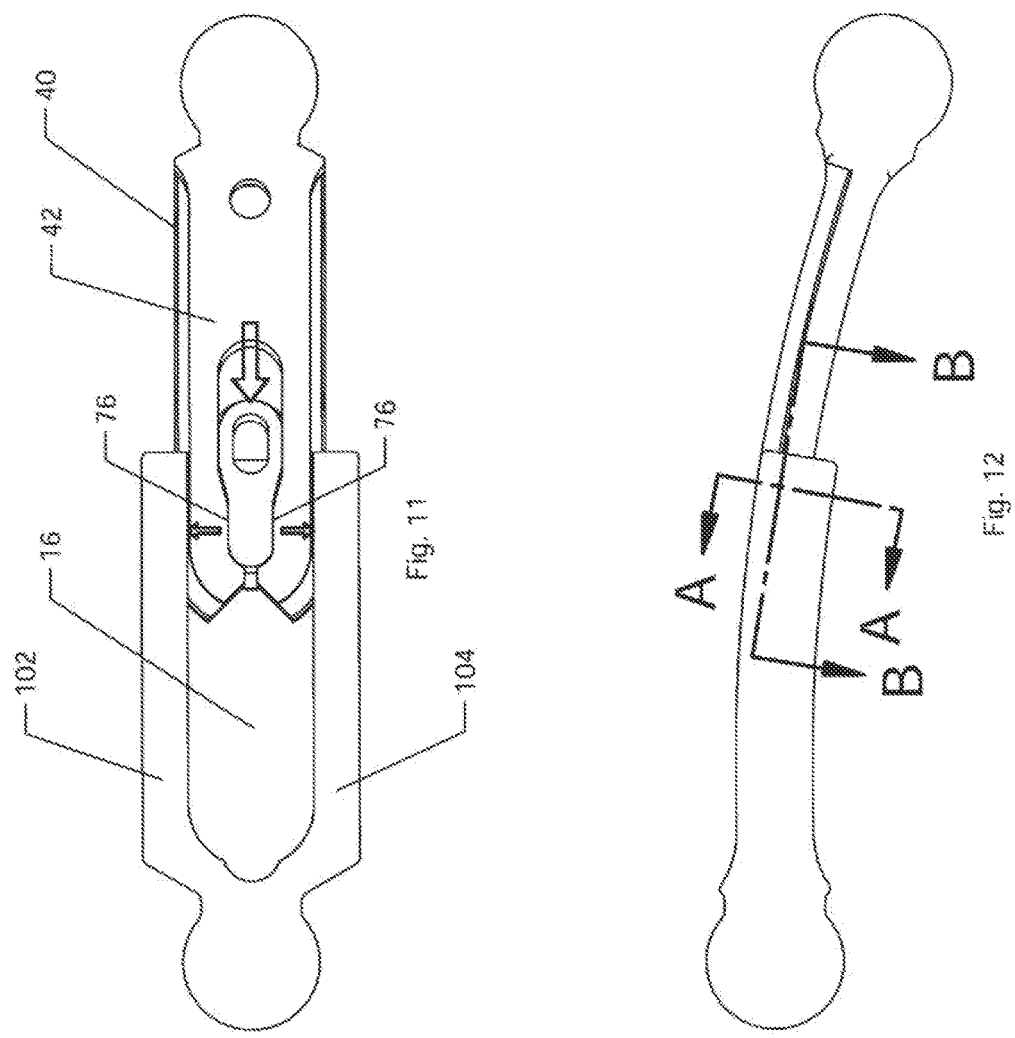

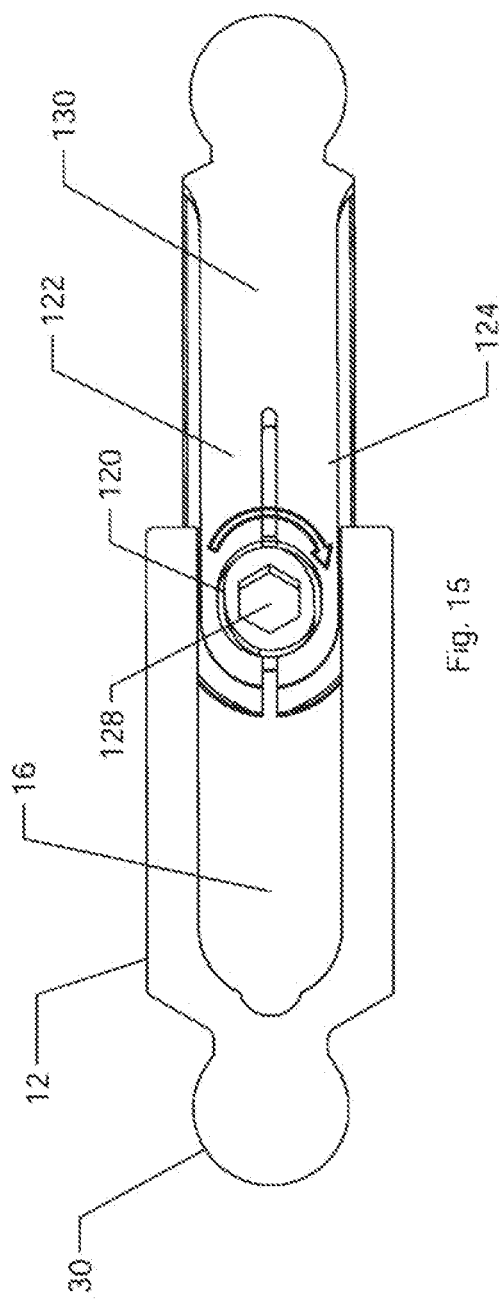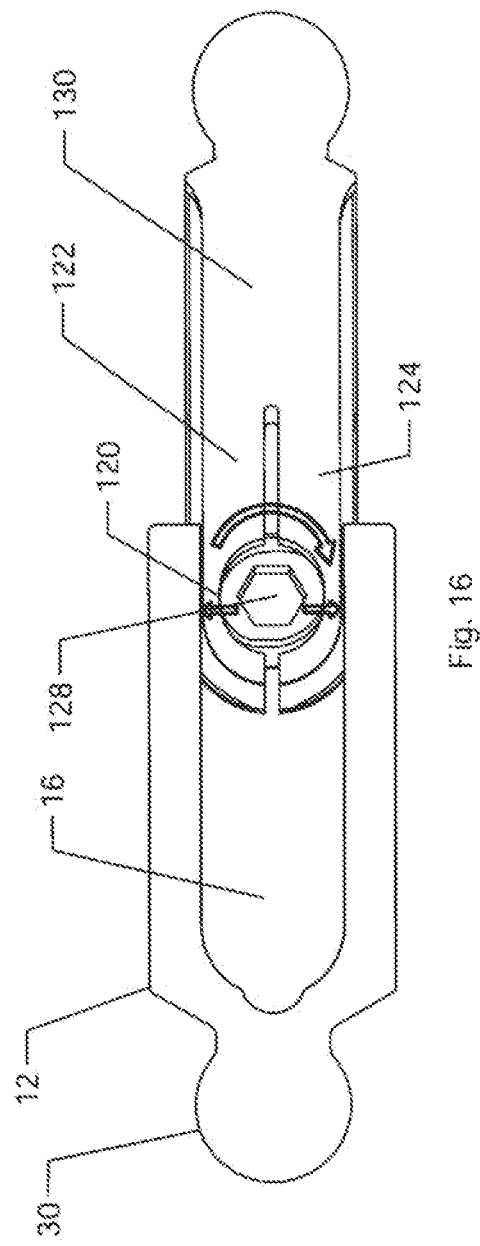

LOW PROFILE ROD-TO-ROD COUPLER

FIELD OF THE INVENTION

The present disclosure is directed to the field of spinal fixation, and specifically, to a low profile coupler for securing adjacent rods together in a fixed relation during spinal correction procedures.

BACKGROUND OF THE INVENTION

Spinal rod systems for use in facilitating spinal fusion, and for correcting and stabilizing spinal curvatures to correct spinal disorders or degenerative conditions, are well known in the art. Spinal rod systems include two or more bone fixation members coupled together with spinal rods. The conventional bone fixation member has a proximal end constructed and arranged to secure to a vertebrae, and a distal end connected to a spinal rod. During a spinal correction procedure, a plurality of fixation members are fixed to vertebrae at various points on each side of the spinal midline. Thereafter, each of the fixation members on each side of the spinal midline is linked with the other fixation members by an elongated spinal rod, such that the spinal rod extends vertically along at least a portion of the length of the spine.

Connector systems for transversely and rigidly connecting adjacent spinal rods together are also well known. Such connector systems are beneficial because they restrict spinal rod migration and increase the overall stiffness of the spinal rod system. In procedures involving multi-level fusion of the spine, a transverse connector system may be essential during the post operative period to minimize the amount of motion permitted between the spinal rods. By providing a rigid transverse connection between adjacent spinal rods, a stiffer construct can be created to enhance the promotion of spinal fusion.

Spinal rods are mounted by a surgeon in a custom-fit manner, both in length and angular positioning. Bending of the rod is common so that the rod is holding the vertebral portions in proper relation. There is not a predetermined distance between two spinal rods, and the rods may converge or diverge from each other. One spinal rod may have a portion directed at an angle different from that of a second other rod.

It is common for the connecting members to have a hook portion extending around a spinal rod and pointing back towards the center of the connecting member. In such an arrangement, installation or implantation of the device requires lateral clearance of the spinal rods so that the hook portion can be placed outside of the spinal rod and then drawn inward for securement on the rod. Often, the patient's soft tissue must be cleared for this purpose; a result which may exacerbate pain, discomfort, and healing time. Many connecting members utilize set screws. For instance, set screws may be utilized for securing a hook type connector, or a U-shaped connector to the spinal rod. The set screw may be utilized for securing one connector end relative to the other.

U.S. Pat. No. 5,947,966 discloses a transverse connector system for linking adjacent spinal rods together. The system includes first and second connector portions which are slidably adjustable in relation to each other. Each connector portion includes an engaging member configured to receive a spinal rod. A wedge member is provided in each engaging member to secure each connector portion to the spinal rod. The wedge member includes a screw for engaging and biasing the spinal rod into a receptacle defined by the engaging member.

U.S. Pat. No. 5,683,392 discloses a multi planar locking mechanism for securing a spinal rod to the spinal column. The locking mechanism includes a bone fixation member for attachment to the bone member, the bone fixation member having a spherical portion; an inner housing member having a channel for receiving the rod and having a spherical portion for engaging the spherical portion of the bone fixation member; and an outer housing member for locking the inner housing member to the rod and the spherical portion of the bone fixation member.

U.S. Pat. No. 6,413,258 discloses a rod-to-rod coupler which includes a body having first and second coupler portions. Each coupler portion defines a concavity configured to receive a portion of an elongated spinal rod. A screw and nut assembly, which includes a screw and a flanged nut, is positioned adjacent each concavity. Each flanged nut has a flange portion which extends at least partially over one concavity.

U.S. Pat. No. 6,113,600 discloses a spinal fixation system having a pair of longitudinal members positionable adjacent the spine, an engaging member for engaging longitudinal members to the spine, a pair of wedge members each having a bearing surface configured to bear on a longitudinal member, and a connector configured to span a distance between the longitudinal members. The connector includes a pair of engaging members each having a fixation surface and a connecting surface, and a bridge member attached to the connecting surfaces.

U.S. Pat. No. 6,238,396 discloses a surgical cross-connecting apparatus for spinal column surgery procedures having rotatable hooking elements with a hook and adjustable securing device, each hooking element is inserted in apertures in one of two elements.

U.S. Pat. No. 7,744,633 discloses a crosslink member for securing spinal rods having connector ends that include a brace and a locking member, each connector includes an arcuate face resting on and securing a spinal rod. The locking member is a cam member that rotates relative to the locking member and engages the connector to displace the cam member. The crosslink includes a male connector with a cylindrical cross rod received by a cavity in a female connector. The cross rod is secured by a pivotable clamp device in the female connector, and the cross rod connector and female connector may pivot, rotate, and telescope relative to each other.

U.S. Pat. No. 10,136,925 discloses a spinal cross-connector having an elongated member, a first connector, and a second connector. The first connector and the second connector are configured to receive spinal rods and adaptable to directly attach with pedicle screws. The first connector includes a first collet head, a first clamp and a first locking means. The second connector includes a second collet head, a second clamp and a second locking means. The first locking means is configured to tighten over a first collet head and engage with the first connector. Similarly, the second locking means is configured to tighten over a second collet head and engage with the second connector. The engagement of the first locking means with the first connector and the second locking means with the second connector locks the spinal cross-connector.

U.S. Pat. RE42,867 discloses an orthopedic device used to fix and stabilize bones to correct anomalies in skeletal structure occurring naturally or by trauma. Bone screws are screwed into bones by application of torque. Clamps are movably attached to the screws. Each clamp includes a compression ring. A connecting rod connects several screws through slots in the clamps. The clamps are tightened to hold the rod and the heads in a pre-selected position by linear movement of the compression rings.

Accordingly, a need exists for an improved spinal rod-to-rod connector system which can be easily and quickly secured between adjacent spinal rods to provide a rigid stabilizing system.

SUMMARY OF THE INVENTION

Disclosed is an ultra-low profile rod-to-rod coupler for connecting adjacent spinal rods. The rod-to-rod coupler consists of an outer bar member having a first end forming a receptacle and a second end available for coupling to a first spinal rod. An inner bar member having a unidirectional insertion end is slidably insertable into the receptacle of the outer bar member, wherein a second end remains available for coupling to a second spinal rod. The insertion end includes a centrally disposed slot bifurcating said insertion end into a left arm and a right arm. A locking member positioned in the centrally disposed slot allows for fixation of the inner bar member to the outer bar member. Placement of the locking member in a first position permits movement of the insertion end within the receptacle. Placement of the locking member in a second position results in splaying the left arm and right arm to frictionally engage an inner sidewall of the receptacle, thereby locking the inner bar member to the outer bar member.

An objective of the invention is to provide an ultra-low profile spinal rod-to-rod coupler for stabilizing adjacent spinal rods.

Another objective of the invention is to provide an adjustable rod-to-rod coupler.

Still another objective of the invention is to provide a rod-to-rod coupler having a unidirectional inner bar member that is insertable in an outer bar member, the inner bar member having a ramp surface constructed and arranged to engage a tab on the outer bar member. The ramp and tab prevent removal of the inner bar member from the outer bar member once inserted.

Yet still another objective of the invention is to provide a rod-to-rod coupler having a slidable locking member to frictionally engage and arrest movement of an inner bar member in relation to an outer bar member, the locking member moved in a slot by use of a pliers.

Yet still another objective of the invention is to provide a rod-to-rod coupler having a rotatable locking member to frictionally engage and arrest movement of an inner bar member in relation to an outer bar member, the locking member rotated in a slot by use of a torque driver.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 9 is a top perspective exploded view of the instant invention;

FIG. 10 is a bottom perspective exploded view thereof;

FIG. 11 is a top view illustrating locker movement;

FIG. 12 is a side view depicting cross-sectional lines;

FIG. 13 is a cross-sectional view taken along lines B-B of FIG. 12;

FIG. 14 is a cross-sectional view taken along lines A-A of FIG. 12;

FIG. 15 is a top view of a second embodiment in its widest position and in an unlocked position; and FIG. 16 is a top view of the second embodiment in its widest position and in a locked position.

DETAILED DESCRIPTION OF THE PREFERRED EMBODIMENT

Figure 1:
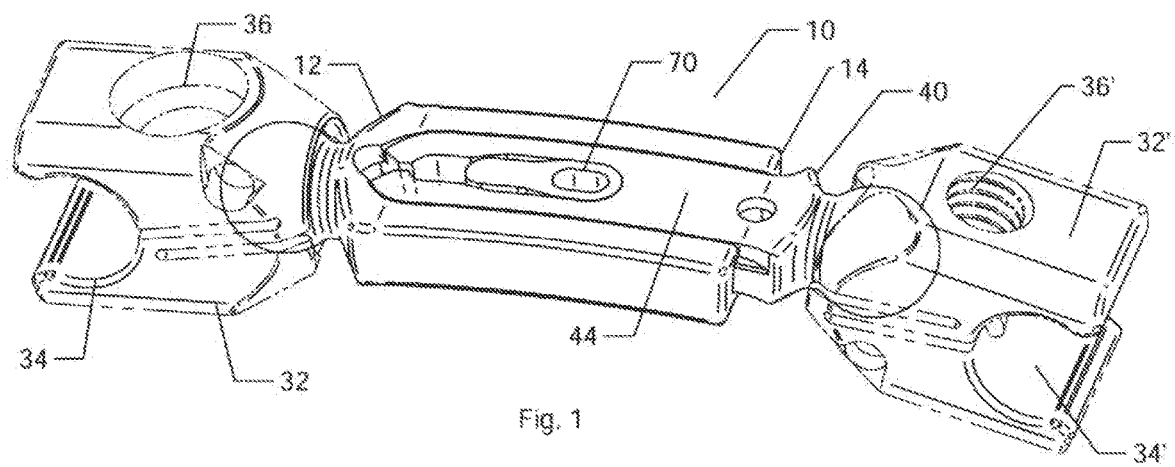
FIG. 1 is a perspective view of the presently disclosed rod-to-rod coupler in its narrowest unlocked position.
Figure 2:
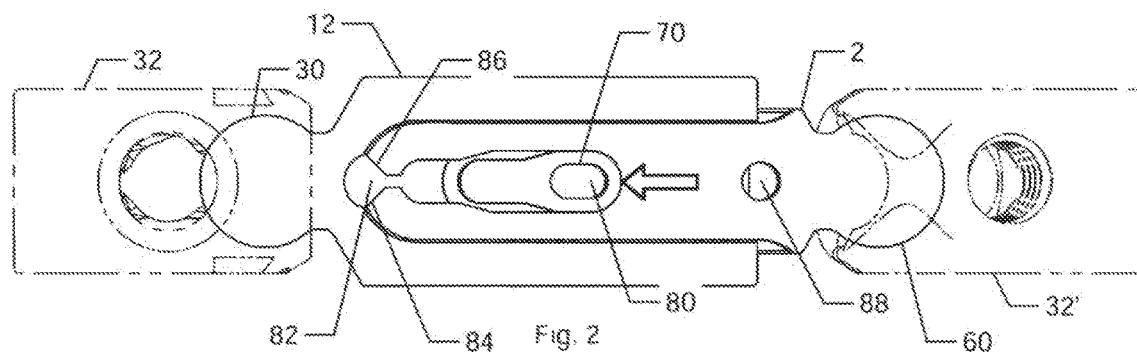
FIG. 2 is a top view of FIG. 1 in an unlocked position.
Figure 3:
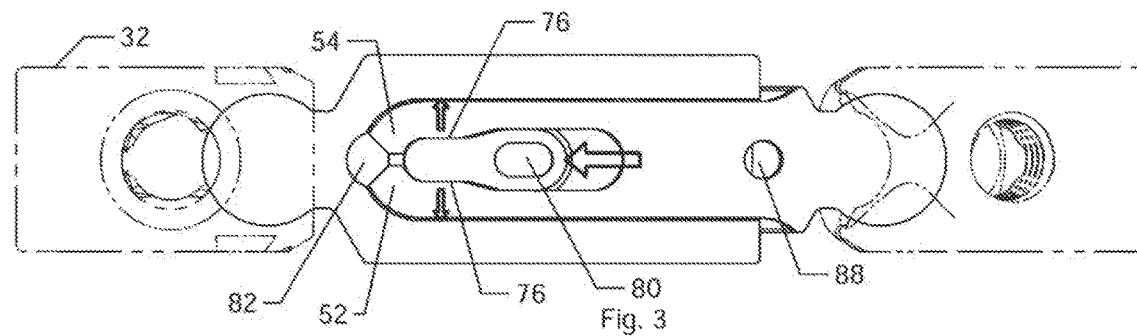
FIG. 3 is a top view of the presently disclosed rod-to-rod coupler in its narrowest locked position.
Figure 4:
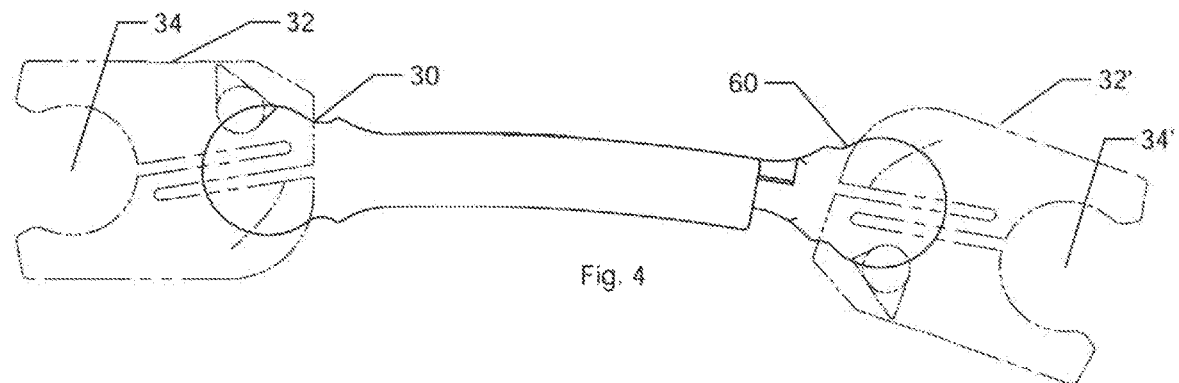
FIG. 4 is a side view of FIG. 3.
Figure 5:
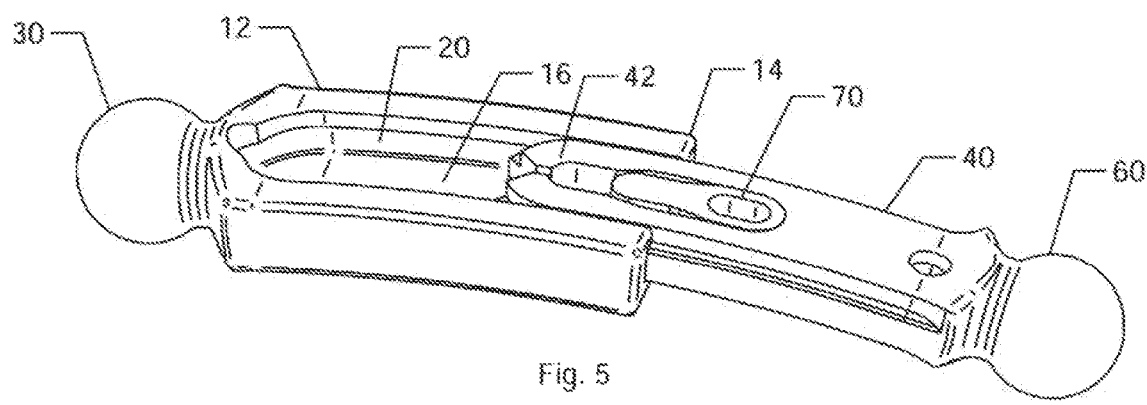
FIG. 5 is a top perspective view of the presently disclosed rod-to-rod coupler in its widest unlocked position.

While the present invention is susceptible of embodiments in various forms, there is shown in the drawings and will hereinafter be described a presently preferred embodiment with the understanding that the present disclosure is to be considered an exemplification of the invention and is not intended to limit the invention to the specific embodiments illustrated.

Referring to the Figures, illustrated is an embodiment of an ultra low profile rod-to-rod coupler 10 for connecting to spinal rods, not shown. The rod-to-rod coupler 10 comprises an outer bar member 12 having a first end 14 forming a receptacle 16 formed from a bottom surface 18, an outer surface 19, first and second side surfaces 20, 22 and upper surfaces 24, 26. A second end 30 is available for coupling to a rod coupler 32, which in turn is secured to a first spinal rod, not shown. The second end 30 depicted is a spherical head. In this embodiment, the second end 30 is illustrated attached to a rod coupler 32 having a U-shaped socket 34 for receipt of a first connector rod, not shown, and a set screw aperture 36 for receipt of a conventional set screw, not shown, used for locking the second end 30 to the first connector rod. The U-shaped rod coupler 32 illustrated may be substituted for a hook-shaped rod coupler or the like.

An inner bar member 40 having a unidirectional insertion end 42 configured and dimensioned to be slidably insertable into the receptacle 16. The insertion end 42 has a top side 44, a bottom side 45, and opposite sides 46, 48. A centrally disposed slot 50 extends between the top side 44 and the bottom side 45; the slot 50 bifurcating the insertion end 42 into a left arm 52 and a right arm 54, wherein each arm 52, 54 has an adjoined proximal end 56 beginning with an edge of the slot 50 and extending to spaced apart tips 57, 58 having an inner surface 62, 64 with each tip having a curved leading edge 66, 68. The space between the tips 57, 58 is identified by numeral 61.

The curved leading edges 66, 68 allow for ease of insertion into the receptacle 16. The opposite end 60 of the inner bar member 40 is spherical shaped and available for coupling to a second rod coupler 32'. The opposite end 60 illustrated is securable to a rod coupler 32' for example purposes. The rod coupler 32' has a socket 34' for receipt of a second connector rod (not shown), and a set screw aperture 36' for receipt of a conventional set screw for use in securing the opposite end 60 to a second connector rod.

Figure 6:
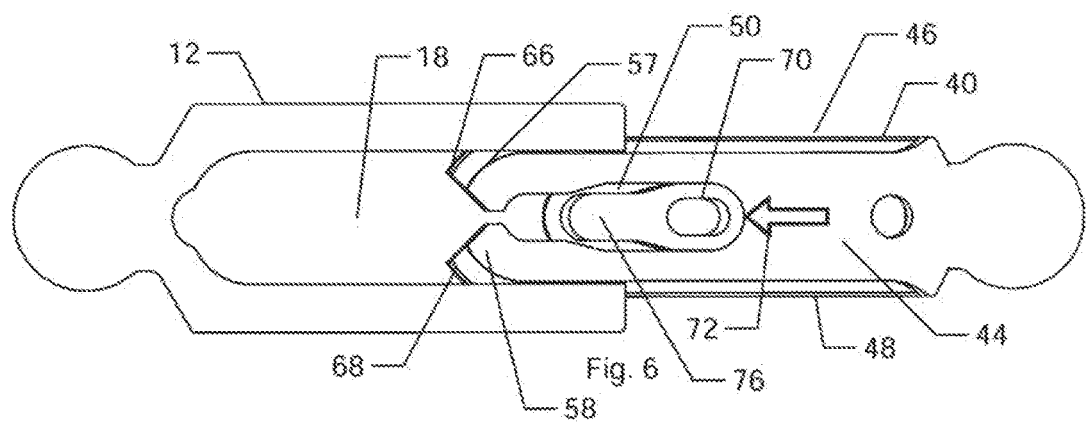
FIG. 6 is a top view of FIG. 5.
Figure 7:
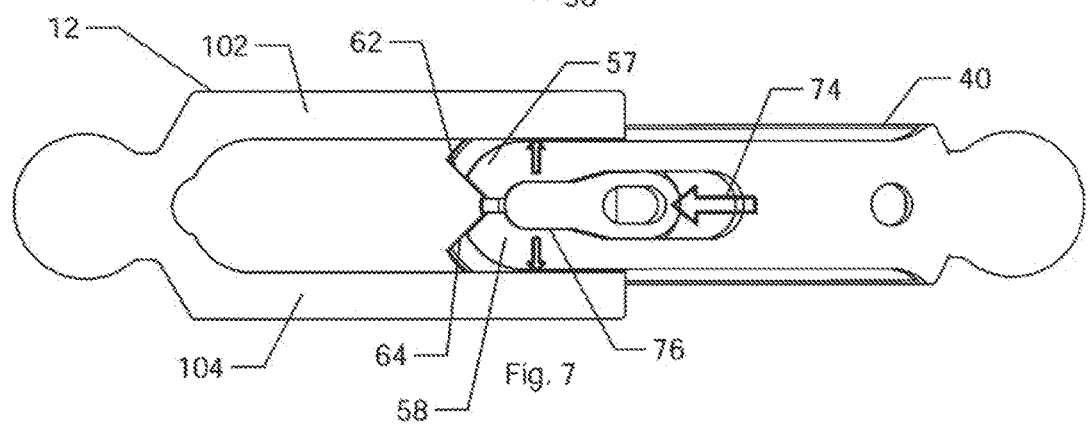
FIG. 7 is a top view of the presently disclosed rod-to-rod coupler in its widest locked position.
Figure 8:
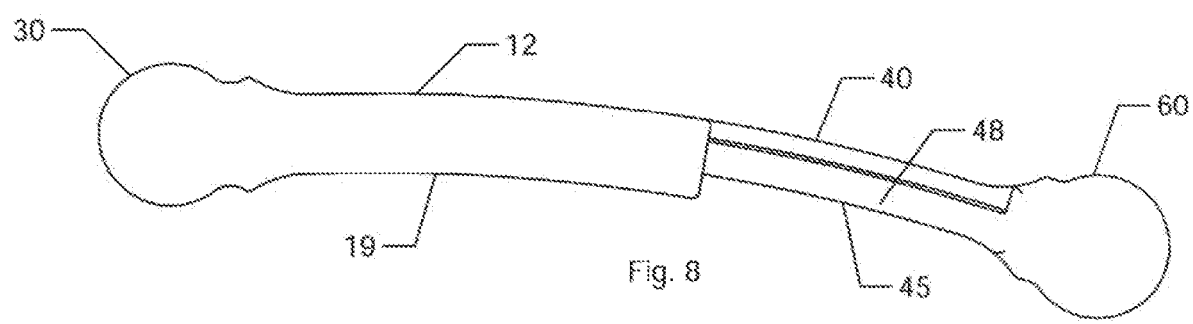
FIG. 8 is a side view of FIG. 7.

A locking member 70 is positioned in the centrally disposed slot 50. The locking member 70 is movable between a first position 72 depicted in FIG. 6, and a second position 74 depicted in FIG. 7. In one embodiment, the locking member 70 is used in an elongated slot, where it is slidable from an unlocked first position 72 to a locked second position 74, whereby the locking member 70 having a wider tongue 76 results in splaying the left arm 52 and the right arm 54 to cause an interference fit with the receptacle 16 sides surfaces 20, 22. Placement of the locking member 70 in the first position 72 permits the movement of the inner bar member 40 within the receptacle 16. Placement of the locking member 70 in the second position 74 results in splaying the left arm 52 and right arm 54 to frictionally engage the sides 20, 22 of the receptacle 16 to stop movement of the inner bar member 40 within the receptacle 16.

For installation, a first opening 80 and a second opening 82 allow receipt of needle nose pliers, not shown. The tips of the pliers are placed within the openings 80, 82, which reduces the pressure required to move the locking member 70 from the unlocked position 72 to the locked position 74. The pliers engage the wedge shaped surface 84, 86, locking the first and second arms 52, 54 against the side surfaces 20, 22 of the receptacle 16 to allow movement without disturbing the position of the inner bar member 40 in relation to the outer member 12. A third opening 88 permits receipt of the pliers tips for moving the locking member 70 from the locked position 74 to an unlocked position 72.

There is an open area 61 when assembling the inner bar member 40 into the outer bar member 12. The opening 61 formed at the front of the inner bar member 40 allows the first and second arms 52, 54 to collapse as it is inserted into the outer bar member 12. The wider portion of the inner bar member 40 contacts the narrower portion of the outer bar member 12, causing a reduction in spacing of the opening 61. After inserting past that area, the inner bar member 40 then springs back to its original shape for the operating range of the device. By returning to the original shape the opening area 61 does not allow the inner bar member 40 and the outer bar member 12 to disengage from each other when used in combination with a lip 90 and ramp 94 described hereafter.

Referring to FIGS. 9-10, the low profile rod-to-rod coupler 10 allows for unidirectional insertion by the inclusion of a lip 90 formed along the inner side wall 20, and a lip 92 formed along the inner side wall 22 of the outer bar member 12; lip 92 forming a mirror image of lip 90. Lip 90 engages a ramp 94 positioned on the right arm 54. Similarly, lip 92 engages a ramp 96 positioned on the left arm 52, ramp 94 forming a mirror image of ramp 96. The spaced apart distal end of the left arm 52 and right arm 54 is constructed and dimensioned to allow temporary inward flexing of said arms 52, 54 along space 61 to allow placement of the insertion end 42 to slide past the lips 90, 92 at the entrance 41 to said receptacle 16, wherein the ramps 94, 96 prevent removal of the inner bar member 40 from the outer bar member 12.

To provide an ultra low profile, a sidewall groove 100 is formed along an upper outer edge of the inner bar member 40. The groove 100 allows a portion of the inner bar member 40 to engage the upper walls 24, 26 of the outer bar member 12, wherein an upper surface 44 of the inner bar member 40 is flush with upper surface 102, 104 of the outer bar member 12. In addition, locking member 70 employs a lower ridge 110 that engages a reciprocal ridge 112 formed on the bottom wall 45 of the inner bar member 40. The lower ridge 110 prevents the locking member 70 from passing through the slot 50. Once the inner bar member 40 is inserted into the outer bar member 12, the bottom 114 of the locking member 70 rests on the bottom surface 18 of the receptacle 16.

FIGS. 15-16 illustrate an alternative embodiment wherein the locker member 120 is oval shaped and rotatable from an unlocked first position shown in FIG. 15, to a locked second position shown in FIG. 16; the locking member 120 splaying the right arm 122 and left arm 124 of the inner bar member 130 to cause an interference fit with the receptacle 16 of the outer bar member 12. The locking member 120 has a torque socket 128 for receipt of a driver, not shown, allowing rotation of the locking member 120. For ease of specification discussion, all other elements of the primary embodiment are incorporated into this alternative embodiment.

The outer bar member 12, the inner bar member 40, and the locking member 70, 120 is formed of titanium or stainless steel.

The term "coupled" is defined as connected, although not necessarily directly, and not necessarily mechanically. The use of the word "a" or "an" when used in conjunction with the term "comprising" in the claims and/or the specification may mean "one," but it is also consistent with the meaning of "one or more" or "at least one." The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

All patents and publications mentioned in this specification are indicative of the levels of those skilled in the art to which the invention pertains. It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures, and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A low profile rod-to-rod coupler for connecting first and second spinal rods, comprising:
   an outer bar member having a first end forming a receptacle with an inner sidewall and a second end available for coupling to the first spinal rod;
   an inner bar having an insertion end configured and dimensioned to be slidably insertable into said receptacle and an opposite end available for coupling to the second spinal rod, said insertion end having a centrally disposed slot bifurcating said insertion end into a left arm and a right arm having spaced apart distal ends; and
   a locking member positioned in said centrally disposed slot, said locking member movable between a first position and a second position;
   wherein placement of said locking member in the first position permits the movement of said insertion end within said receptacle, and placement of said locking member in the second position forces said left arm and said right arm to frictionally engage said inner sidewall of said receptacle to stop movement of said insertion end within said receptacle; wherein a center of locking member in the first position is closer to the opposite end of the inner bar than the center of the locking member in the second position.

2. The low profile rod-to-rod coupler according to claim 1, wherein said locking member is elongated and slidable from the first position to the second position, whereby said locking member has a wider tongue for splaying said left arm and said right arm to cause an interference fit with said receptacle inner sidewall.

3. The low profile rod-to-rod coupler according to claim 1 wherein said insertion end is constructed and arranged for unidirectional insertion into said receptacle.

4. The low profile rod-to-rod coupler according to claim 1 wherein said insertion end is further defined by a top side, a bottom side with said centrally disposed slot extending between the top and bottom side, said slot bifurcating said insertion end into said left arm and a right arm, wherein each said arm having an adjoined proximal end beginning with an edge of said slot.

5. The low profile rod-to-rod coupler according to claim 4 wherein said outer bar member includes a lip formed along said inner sidewall at an entrance to said receptacle, said lip engaging a ramp positioned on the distal ends of said left arm and said right arm to inhibit removal of said insertion end of said inner bar from said receptacle of said outer bar member.

6. The low profile rod-to-rod coupler according to claim 5 wherein said spaced apart distal ends of said left and right arms are constructed and dimensioned to allow temporary inward flexing of said arms to allow placement of said insertion end to slide past the lip at the entrance to said receptacle.

7. The low profile rod-to-rod coupler according to claim 1 wherein a leading edge of said left arm and right arm are curved for ease of insertion into said receptacle.

8. The low profile rod-to-rod coupler according to claim 1 wherein said insertion end of said inner bar includes a groove formed along an outer wall of said left arm and said right arm, said groove constructed and arranged to engage an upper wall of said outer bar member, wherein an upper surface of said insertion end is flush with an upper surface of said upper wall.

9. The low profile rod-to-rod coupler according to claim 1 wherein said locking member includes a lower edge forming a rim constructed and arranged to engage a lower side surface of said insertion end, wherein said rim is secured between the lower side surface and the receptacle.

10. The low profile rod-to-rod coupler according to claim 1 wherein said second end of said outer bar member and said opposite end of said inner bar member are spherical.

11. A low profile rod-to-rod coupler for connecting first and second spinal rods, comprising:
    an outer bar member having a first end forming a receptacle with an inner sidewall and a second end available for coupling to the first spinal rod;
    an inner bar having a unidirectional insertion end configured and dimensioned to be slidably insertable into said receptacle and an opposite end available for coupling to the second spinal rod, said insertion end having a top side, a bottom side, and a centrally disposed slot extending between the top and bottom side, said slot bifurcating said insertion end into a left arm and a right arm, wherein each said arm has an adjoined proximal end beginning with an edge of said slot and extending to a spaced apart distal end; and
    a locking member positioned in said centrally disposed slot, said locking member movable between a first position and a second position;
    wherein placement of said locking member in the first position permits the movement of said insertion end within said receptacle, and placement of said locking member in the second position splaying said left arm and said right arm to frictionally engage said inner sidewall of said receptacle to stop movement of said insertion end within said receptacle; wherein a center of locking member in the first position is closer to the opposite end of the inner bar than the center of the locking member in the second position.

12. The low profile rod-to-rod coupler according to claim 11 wherein said locking member is elongated and slidable from the first position to the second position, whereby said locking member having a wider tongue for splaying said left arm and said right arm to cause an interference fit with said receptacle inner sidewall.

13. The low profile rod-to-rod coupler according to claim 11, wherein said outer bar member includes a lip formed along said inner sidewall at an entrance to said receptacle, said lip engaging a ramp positioned on the distal ends of said left arm and said right arm to inhibit removal of said insertion end of said inner bar from said receptacle of said outer bar member.

14. The low profile rod-to-rod coupler according to claim 13 wherein said spaced apart distal ends of said left arm and right arm are constructed and dimensioned to allow temporary inward flexing of said arms to allow placement of said insertion end to slide past the lip at the entrance to said receptacle.

15. The low profile rod-to-rod coupler according to claim 14 wherein a leading edge of said left arm and right arm are curved for ease of insertion into said receptacle.

16. The low profile rod-to-rod coupler according to claim 11 wherein said insertion end of said inner bar includes a groove formed along an outer wall of said left arm and said right arm, said groove constructed and arranged to engage an upper wall of said outer bar member, wherein said top side of said insertion end is flush with an upper surface of said upper wall.

17. The low profile rod-to-rod coupler according to claim 11 wherein said second end of said outer bar member and said opposite end of said inner bar are spherical.

18. The low profile rod-to-rod coupler according to claim 11 wherein said outer bar member, said inner bar, and said locking member are formed of titanium.

19. The low profile rod-to-rod coupler according to claim 11 wherein said outer bar member, said inner bar, and said locking member are formed of stainless steel.

\* \* \* \* \*